United States Patent [19]

Stiegler

[11] Patent Number: 4,553,534
[45] Date of Patent: Nov. 19, 1985

[54] APPARATUS FOR RELIEVING PSYCHOLOGICAL STRESS

[76] Inventor: Reinhard Stiegler, Breitenseerstrasse 108/7, A-1140 Wien, Austria

[21] Appl. No.: 505,059

[22] Filed: Jun. 16, 1983

[30] Foreign Application Priority Data

Jun. 16, 1982 [AT] Austria .................................. 2332/82

[51] Int. Cl.$^4$ ............................................ A61M 21/00
[52] U.S. Cl. .................... 128/24.1; 128/1 R
[58] Field of Search ..................... 128/24.1, 1 R, 1 C; 352/63; 434/43, 41; 351/155, 156; 455/149; 179/146 R

[56] References Cited

U.S. PATENT DOCUMENTS

| | | | |
|---|---|---|---|
| 3,014,477 | 12/1961 | Carlin | 128/1 C |
| 3,207,847 | 9/1965 | Epstein | 128/1 C |
| 3,512,088 | 5/1970 | Ross | 455/149 |
| 3,568,211 | 3/1971 | Petruzella, Jr. | 2/6 |
| 3,822,693 | 7/1974 | King | 128/1 C |
| 3,908,634 | 9/1975 | Monaghan | 128/1 C X |
| 3,950,086 | 4/1976 | Schulman et al. | 128/1 C X |
| 4,289,121 | 9/1981 | Kupriyanovich | 128/1 C |
| 4,315,502 | 2/1982 | Gorges | 128/1 C |

OTHER PUBLICATIONS

*Avionics*, "Navy Studies Helmet-Mounted Display" from Aviation Week & Space Technology (5-16-77).

Primary Examiner—Robert A. Hafer
Assistant Examiner—Danton DeMille
Attorney, Agent, or Firm—Karl F. Ross; Herbert Dubno

[57] ABSTRACT

An apparatus for treating stress has a support shaped to fit on the head and constructed to shield the ears from external noise, a display carried on the support and positionable in front of the wearer's eyes, sound transducers in the support positioned to be juxtaposed with the wearer's ears, and a recorder and amplifier for activating the transducers and display with stress-reducing sounds and images. A visor forming the display is pivoted on the support so it can be moved out of the wearer's line of sight. The display itself can be a television-type screen, a multiplicity of light-emitting diodes, or a transparency or slide-type projection arrangement. The support can be a head-encasing helmet of the type worn in football or could be a pair of ear-covering stereophonic headphones carrying a visor provided with the display.

6 Claims, 4 Drawing Figures

APPARATUS FOR RELIEVING PSYCHOLOGICAL STRESS

FIELD OF THE INVENTION

The present invention relates to the treatment of psychological stress. More particularly this invention concerns an apparatus for relieving such stress.

BACKGROUND OF THE INVENTION

Emotional, psychological stress caused by the increasing pace and demands of modern life is rapidly becoming a serious medical problem. Many somatic ailments, such as circulatory hypertension, are rooted in such stress, and other apparently organic problems, such as migraine headaches, are sometimes aggravated or wholly caused by it.

Various techniques for relieving stress involve some form of relaxation, often with the intention of creating a physical and emotional state corresponding to that of a trance or deep meditation. Special sensory-deprivation chambers in which the patient or subject is wholly without external stimulus have proven quite effective in reducing stress-related symptoms. Unfortunately this type of device available to treat stress or assist stress-relief therapy is usually so cumbersome and expensive as to put such treatment out of reach to the majority.

OBJECTS OF THE INVENTION

It is therefore an object of the present invention to provide an improved apparatus for treating stress.

Another object is the provision of such an apparatus for treating stress which overcomes the above-given disadvantages, that is which operates effectively but which is convenient to use and relatively inexpensive.

SUMMARY OF THE INVENTION

An apparatus for treating stress according to the invention has a support shaped to fit on the head and constructed to shield the ears from external noise, a display carried on the support and positionable in front of the wearer's eyes, sound transducers in the support positioned to be juxtaposed with the wearer's ears, and means for activating the transducers and display with stress-reducing sounds and images.

This arrangement therefore is completely portable, can be produced at relatively low cost, and is easy to use. The activating means usually includes a player, typically with magnetic-tape storage, that creates stress-relieving sounds and images. Typically various colors have been found to induce the desired relaxation response. The activating means of the invention is a tape player mounted in the support, which is according to another feature of this invention a head-encasing helmet of the type worn in football or in vehicular sports. The support could also be built as a pair of ear-covering stereophonic headphones carrying a visor provided with the display.

The visor forming the display is pivoted on the support according to this invention so it can be moved out of the wearer's line of sight. Normally it completely covers the wearer's eyes when down in place, completely blocking out external visual stimulus.

The display itself according to this invention can be a television-type screen, of the so-called flat type which finds particular utility with the instant invention since its major drawback—low light level—is unimportant in the wholly dark helmet interior. The display can similarly be formed of a multiplicity of light-emitting diodes. It is also possible to use a transparency or slide-type projection arrangement, in particular when nothing other than a particular color field is to be displayed.

DESCRIPTION OF THE DRAWING

The above and other features and advantages will become more readily apparent from the following, reference being made to the accompanying drawing in which.

SPECIFIC DESCRIPTION

Figure 1:
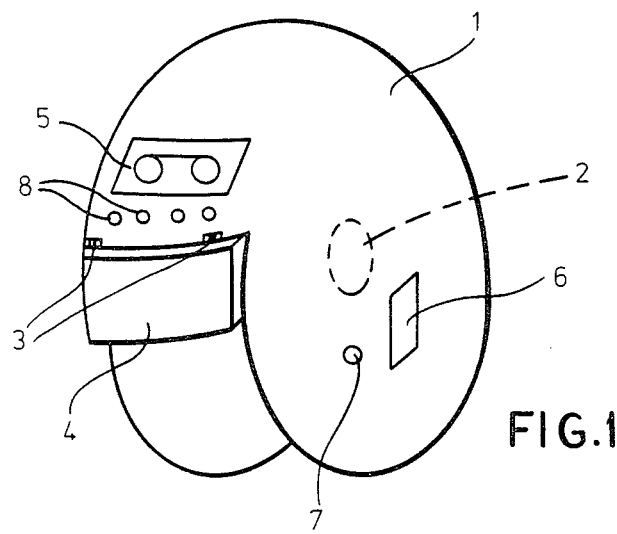
FIG. 1 is a perspective view of a helmet-type device according to the invention.

As seen in FIG. 1 a helmet 1 according to this invention is of the bubble motorcycle type, and is suitably insulated and fitted to the user that it substantially completely blocks out external sound. It is provided internally with small sound transducers, here high-fidelity miniature loudspeakers 2, positioned to lie at the user's ears and provide true stereophonic separation.

A visor 4 is connected at hinges 3 so that it can lie directly in front of the wearer's eyes, or pivoted up out of the way when donning and removing the device. This visor 4 is constituted as a television-type video display of the flat semiconductor type capable of reproducing images and color.

A cassette-type sound and video recorder 5 powered either from batteries 6 in the helmet 1 or from a plug-in line connection 7 feeds a stress-reducing sound program to the speakers 2 and a stress-inducing picture to the display visor 4.

A typical such program would start with calming words together with orange spots of light. Then the color would go to green and then to blue. As the light spots appear calming music and finally speech is played while the light intensity varies with the sound level so that loud notes correspond to bright lights and soft notes to dim ones. Toward the end of the stress-relieving program the color of the light spots returns to orange and terminates at red. Other programs can serve self-hypnosis purposes, assist meditation, or otherwise relieve stress.

Figure 3:
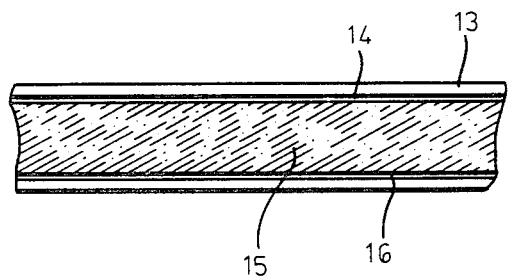
FIG. 3 is a large-scale view of a magnetic video tape according to the invention.

Such a program can be carried on a magnetic tape 13 such as shown in FIG. 3. This tape 13 has a central region 15 carrying a diagonally recorded picture, one edge 14 carrying an audio track, and an opposite edge 16 carrying control signals.

Figure 2:
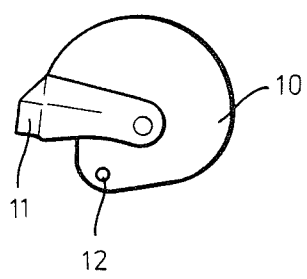
FIG. 2 is a small-scale side view of another such device in accordance with this invention.

The arrangement of FIG. 2 has a helmet 10 with a projector-type visor display 11 that is powered through a line plug. In this arrangement color fields of various colors are projected onto the inside of the visor 11, without forming images. Just by using four different transparencies, it is possible to achieve a complete spectrum.

Figure 4:
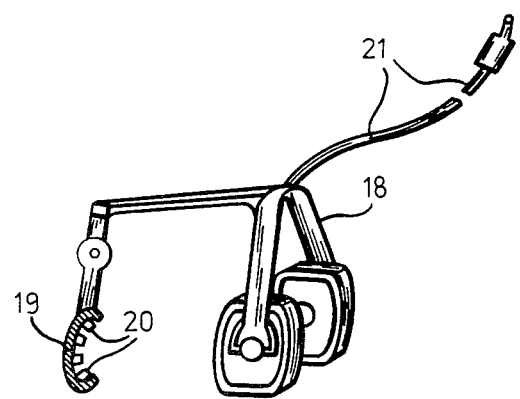
FIG. 4 is a partly sectional side view of a further device according to the present invention.

FIG. 4 shows yet another arrangement formed as a pair of ear-encasing earphones 18 carrying a screen 19 formed by a multiplicity of light-emitting diodes. A plug-carrying wire 21 allows the unit to be plugged into a standard or specially adapted video/audio recorder.

The screen 19 here is shaped like a sleep mask to cover the eyes and block out all external light.

What is claimed is:

1. An apparatus for treating stress, the apparatus comprising:
    a support in the form of a helment shaped to fit on the head and constructed to shield the ears from external noise;
    a visible display carried on the support and pivotable into a position in which it completely blocks out external visual stimulus;
    sound transducers in the support positioned to be juxtaposed with the wearer's ears; and
    means including a tape player mounted in the support, said tape player having means for activating the transducers and display providing stress-reducing sounds and images.

2. The stress-treating apparatus defined in claim 1 wherein the display is formed as a visor movable out of the wearer's line of sight.

3. The stress-treating apparatus defined in claim 1 wherein the display is constituted as a television screen.

4. The stress-treating apparatus defined in claim 1 wherein the display has a multiplicity of light-emitting diodes.

5. The stress-treating apparatus defined in claim 1 wherein the activating means includes an amplifier connected to the transducers.

6. The stress-treating apparatus defined in claim 1, wherein the activating means includes means for making different colors appear on the display.

* * * * *